United States Patent [19]

Chen et al.

[11] 4,082,881

[45] Apr. 4, 1978

[54] TOPICAL AND OTHER TYPE PHARMACEUTICAL FORMULATIONS CONTAINING ISOSORBIDE CARRIER

[75] Inventors: James Ling Chen, East Brunswick; Jean M. Battaglia, North Brunswick, both of N.J.

[73] Assignee: E. R. Squibb & Sons, Inc., Princeton, N.J.

[21] Appl. No.: 753,969

[22] Filed: Dec. 23, 1976

[51] Int. Cl.² ............................................. A61K 31/58
[52] U.S. Cl. ................................................... 424/241
[58] Field of Search ................................ 424/241, 243

[56] References Cited

U.S. PATENT DOCUMENTS

| | | | |
|---|---|---|---|
| 3,457,348 | 7/1967 | Nash et al. | 424/241 |
| 3,592,930 | 7/1971 | Katz et al. | 424/241 |

*Primary Examiner*—Elbert L. Roberts
*Attorney, Agent, or Firm*—Lawrence S. Levinson; Merle J. Smith; Burton Rodney

[57] ABSTRACT

Topical and other type formulations are provided in the form of creams, lotions, ointments, injectables, and drops which contain a pharmaceutical, such as a steroid, dissolved in an isosorbide solvent system.

15 Claims, No Drawings

TOPICAL AND OTHER TYPE PHARMACEUTICAL FORMULATIONS CONTAINING ISOSORBIDE CARRIER

The present invention relates to pharmaceutical formulations which include one or more isosorbides, such as dimethylisosorbide, as a vehicle for the pharmaceutical.

Topical steroid formulations containing 21-chloro-9α-fluoro-Δ⁴-pregnene-11β,16α,17α-triol-3,20-dione 16,17-acetonide as the active ingredient are extensively employed in the treatment of skin disorders, such as dermatitis. To be therapeutically effective, the active ingredient must be in a molecular dispersion to facilitate desired percutaneous absorption which is particularly important in achieving a therapeutic response for the management of psoriasis. Unfortunately, the above steroid is insoluble in water (less than 0.0005% soluble) and is even less soluble in hydrocarbon vehicles such as mineral oil, petrolatum or polyethylene gelled mineral oil. Various organic solvents and solubilizers have been found to be good solvents for such steroid. However, they have been found to be unsuitable for commercial application for reasons such as their high volatility and low boiling points, their disagreeable odor, their "paint removing" property, and their undesirable skin reaction. Furthermore, various water-soluble emulsifiers and oil liquids or emollients have been suggested for use in preparing ointments, gels, creams and lotions. However, because of the undesirably low solubility of the steriod in such vehicles, higher levels of these materials in topical products are required thereby increasing their cost and also adversely affecting their cosmetic elegance.

Accordingly, in view of the above considerations, it is seen that a need exists for a suitable vehicle capable of solubilizing a sufficient amount of the steroid so that it may be employed in a topical formulation, while being dermatologically beneficial, stable, and pharmaceutically acceptable.

In accordance with the present invention, it has now been found that isosorbides, such as dimethylisosorbide, are excellent vehicles for 21-chloro-9α-fluoro-Δ⁴-pregnene-11β,16α,17α-triol-3,20-dione 16,17-acetonide as well as for other steroids such as 21-chloro-9-fluoro-2',3'-dihydro-11β-hydroxy-5'-phenylpregna-1,4-dieno[16α,17-b][1,4]dioxin-3,20-dione acetone solvate or dichloro methane solvate (1:1), 9α-fluoro-11β,17,21-tetrahydroxy-pregna-1,4-diene-3,20-dione 16,17-acetonide, progesterone, and testololactone.

The active ingredient employed in the formulations of the invention will preferably comprise a steroid which will be present in an amount of from about 0.001 to about 3% by weight, and preferably from about 0.025 to about 0.2% based on the total weight of the composition, depending upon the type of steroid employed and its solubility in the isosorbide containing vehicle. As will be seen hereinafter, other active ingredients may be employed in conjunction with or in lieu of the steriod. In such case, the other active ingredients, such as econazole, including the free base and salts thereof, miconazole, griseofulvin, nystatin, neomycins, gramicidins, and the like, and mixtures thereof, may be employed in amounts up to and even greater than 3%.

The isosorbide vehicle employed in the formulations of the invention will have the structure

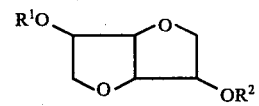

wherein $R^1$ and $R^2$ can be the same or different and are hydrogen or lower alkyl containing 1 to 5 carbons, with at least one of $R^1$ and $R^2$ being lower alkyl. Examples of isosorbides suitable for use herein include, but are not limited to, dimethylisosorbide, diethylisosorbide, ethylmethylisosorbide, dipropylisosorbide, or mixtures thereof.

The isosorbide will be present in the compositions of the invention in amounts within the range of from about 0.5 to about 95% and more depending upon the type of pharmaceutical composition and the active ingredient contained therein.

The formulations employing the isosorbide vehicle in accordance with the present invention may take the form of an ointment (non-aqueous), cream, lotion, as well as a liquid including parenterals (including injectables), eye drops, nose drops, ear drops and the like.

The lotion or cream includes a relatively large aqueous isosorbide phase and a relatively small oil phase. The lotions and creams of the invention will include the active ingredient "all-in-solution" so that substantially no active ingredient crystallizes out at room temperature.

With regard to the cream formulations of the invention where the steroid is to be all-in-solution, the cream will contain from about 0.005 to about 0.6% and preferably from about 0.025 to about 0.2% by weight of the active ingredient based on the weight of the entire cream formulation, and from about 30 to about 75% and preferably from about 35 to about 65% by weight of the isosorbide based on the weight of the entire cream formulation and depending upon the solubility of the particular active ingredient in the particular isosorbide employed. The all-in-solution cream formulation will include substantially all of the active ingredient in the aqueous-isosorbide phase; however, small amounts of the active ingredient may be present in the oil phase as well. In addition, the all-in-solution cream formulation will also include in the oil phase, from about 5 to about 14% and preferably from about 8 to about 12% by weight of the emulsifier-thickener based on the weight of the entire cream formulation, and from about 2 to about 8% and preferably from about 3 to about 5% by weight of oleaginous material or emollient based on the weight of the entire cream formulation. The oil phase may also optionally include an anti-whitening agent or anti-foaming agent in an amount within the range of from about 0.2 to about 3% and preferably from about 0.5 to about 1.5% by weight based on the entire cream formulation. An antioxidant may also optionally be included in an amount within the range of from about 0.005 to about 0.04% and preferably from about 0.01 to about 0.03% by weight based on the entire cream formulation.

The aqueous phase of the all-in-solution cream formulation may contain a glycol type preservative such as propylene glycol in an amount within the range of from about 5 to about 50% and preferably from about 15 to about 40% by weight of the entire cream formulation and/or a paraben or other conventional type perservative such as methyl and/or propyl paraben in an amount ranging from about 0.05 to about 0.5%, and purified water in an amount within the range of from about 30 to about 70% by weight and preferably from about 35 to about 65% by weight of the entire cream formulation.

With regard to the lotion formulation of the invention where the steroid is to be all-in-solution, the lotion will contain from about 0.005 to about 0.6% and preferably from about 0.025 to about 0.2% by weight of the active ingredient based on the weight of the entire lotion formulation, and from about 30 to about 75% and preferably from about 35 to about 65% by weight of the isosorbide based on the weight of the entire lotion formulation, depending upon the solubility of the particular active ingredient in the particular isosorbide employed. The active ingredient in the all-in-solution lotion formulation can have part of it also solubilized in the oil phase. The lotion may contain from about 5 to about 14% and preferably from about 8 to about 12% by weight emulsifier-thickener based on the weight of the entire lotion formulation, and from about 0.5 to about 6% and preferably from about 1 to about 5% by weight of oleaginous material or emollient based on the weight of the entire lotion formulation. The oil phase may also optionally include an anti-whitening agent or anti-forming agent in an amount within the range of from about 0.2 to about 3% and preferably from about 0.5 to about 1.5% by weight based on the entire lotion formulation. An antioxidant may also opeionally be included in an amount within the range of from about 0.005 to about 0.04% and preferably from about 0.01 to about 0.03% by weight based on the entire lotion formulation.

The aqueous phase of the all-in-solution lotion formulation may contain a glycol-type preservative in an amount within the range of from about 5 to about 50% and preferably from about 15 to about 40% by weight of the entire lotion formulation, and/or paraben or other conventional type preservative in an amount ranging from about 0.05 to about 0.5%, and purified water in an amount within the range of from about 90% by weight and preferably from about 60 to about 85% by weight of the entire lotion formulation.

Where the active ingredient is to be employed in parenteral solutions, the isosorbide vehicle will be present in amounts ranging from about 40 to about 95%, and preferably from about 50 to about 90%; the concentration of active ingredient will vary depending upon the type employed. In the case of steroids, it may be employed in amounts ranging from about 0.01 to about 2.5% by weight.

When the formulation of the invention is in the form of eye drops, nose drops or ear drops, the isosorbide vehicle will be present in amounts ranging from about 25 to about 60% and preferably from about 35 to about 45% by weight while the active ingredient will vary depending upon the type used.

With regard to specific steroid formulations, where 2-chloro-9α-fluoro-Δ$^4$-pregnene-11β,16α,17α-triol-3,20-dione 16,17-acetonide is employed in all-in-solution creams or lotions, the isosorbide vehicle will be preferably employed in an amount within the range of from about 30 to about 70% by weight and more preferably within the range of from about 40 to about 60% by weight, while the steroid will be present in amounts ranging from about 0.02 to about 0.2% by weight.

Where 9α-fluoro-11β,17,21-tetrahydroxypregna-1,4-diene-3,20-dione 16,17-acetonide is employed in all-in-solution creams or lotions, the isosorbide vehicle will be preferably employed in an amount within the range of from about 30 to about 50% by weight and more preferably within the range of from about 35 to about 45% by weight while the steroid will be employed in amounts ranging from about 0.02 to about 0.2% by weight.

Where other active ingredients (as described above) are employed in a cream or lotion, the isosorbide vehicle will be preferably employed in amounts within the range of from about 30 to about 65% by weight and preferably from about 40 to about 60% by weight while the active ingredient will vary depending upon its type. Where steroids are to be used they may be employed in amounts within the range of from about 0.001 to about 2% by weight.

The ointment formulations of the invention comprise a steroid or other pharmaceutical as described herein, an isosorbide vehicle and oleaginous material, and optionally a wax.

The term "ointment" or "ointment formulation" as employed herein includes non-aqueous formulations such as gels, ointments, lipophilic sticks, and the like.

The oleaginous material will generally be present in an amount within the range of from about 30 to about 99% by weight, and preferably from about 50 to about 90% by weight.

The ointments of the invention may include the active ingredient solubilized in both the isosorbide or isosorbide-aqueous phase and in the oil phase. The percentage of water in isosorbide-aqueous phase may vary from about 5 to about 20% of the ointment.

The ointment will contain from about 0.001 to about 2%, and preferably from about 0.025 to about 0.2% by weight of the steroid ingredient, and from about 0.5 to about 75% and preferably from about 5 to about 65% by weight of the isosorbide based on the weight of the entire ointment formulation (and up to 75% by weight isosorbide in the case of the lipophilic stick) and depending upon the solubility of the particular active ingredient in the particular isosorbide employed. The all-in-solution ointment formulation (exclusive of the gel and lipophilic stick) will also include, in addition to the active ingredient and isosorbide, from about 85 to about 99% and preferably from about 85 to about 95% by weight of oleaginous material based on the weight of the entire formulation. The formulation may also optionally include an opacifying agent, such as titanium dioxide, serving as indicator for homogeneity of dispersion, in an amount within the range of from about 0.2 to about 1% and preferably from about 0.3 to about 0.8% by weight based on the entire formulation. An antioxidant may also optionally be included in an amount within the range of from about 0.005 to about 0.04% and preferably from about 0.1 to about 0.03% by weight based on the entire formulation.

Examples of oleaginous material suitable for use herein are petrolatum, other isosorbide immiscible oily material and mineral oil thickened or gelled with polyethylene, or high molecular weight paraffin waxes or mono and diglycerides of fatty acids gelled with high molecular weight fatty acids and/or polyamide complex of hydroxystearate. Petrolatum (petroleum jelly) is a purified mixture of semisolid hydrocarbons from petroleum having a melting point of from about 45° to about 65° C, preferably from about 50° to about 60° C. When the mixture of active ingredient and isosorbide is mechanically dispersed in the oleaginous material, the latter may be mineral oil thickened with polyethylene as disclosed in U.S. Pat. Nos. 2,627,938, 2,628,187, 2,628,205 and 3,733,403. The disclosures of the foregoing patents are incorporated herein by reference.

The all-in-solution ointment may simply be prepared by dissolving the active ingredient in the isosorbide with gentle heat not over 90° C, cooling to room temperature and then incorporating the same into the oleaginous material by slow mixing until homogeneous.

The gel formulation of the invention is preferably in the form of a lipophilic clear gel, and will contain from about 0.005 to about 3%, and preferably from about 0.025 to about 0.5% by weight of the active ingredient (where a steroid) based on the weight of the entire formulation, and from about 0.5 to about 20% and preferably from about 1 to about 10% by weight of the isosorbide based on the weight of the entire formulation, depending upon the solubility of the particular active ingredient in the particular isosorbide employed. The gel formulation will also include from about 75 to about 94% and preferably from about 80 to about 90% by weight of the oleaginous material. The formulation may also optionally include a surfactant, such as Span 65 (sorbitan tristearate), as well as Span 60 (sorbitan monostearate), Span 40 (sorbitan monopalmitate), butylene glycol distearate in amounts up to about 8% by weight based on the entire formulation. An antioxidant, such as butylated hydroxyanisole or butylated hydroxytoluene may also optionally be included in amounts up to about 0.1% and preferably up to about 0.05% by weight based on the entire formulation.

In the non-aqueous gel formulation of the invention, the oleaginous material includes mineral oil gelled with waxes such as high molecular weight pariffin wax (Paraflint RG), mono and diglycerides of fatty acids such as Arlacel 186 (Atlas Co.) as well as propylene glycol isostearate (Emery 2389A) or isostearyl alcohol (Adol 66), gelled with high molecular weight fatty acids such as Emery 865A, (Emery Industries) and/or polyamide complex of hydroxystearate (Acrowax, Glyco).

With regard to specific steroid ointment or gel formulations, where 21-chloro-9α-fluoro-Δ⁴-pregnene-11β,16α,17α-triol-3,20-dione 16,17-acetonide is employed in all-in-solution ointments, the isosorbide vehicle will be preferably employed in an amount within the range of from about 10 to about 25% by weight and more preferably within the range of from about 15 to about 25% by weight, while the steroid will be employed in amounts ranging from about 0.001 to about 1% by weight.

Where 21-chloro-9-fluoro-2',3'-dihydro-11β-hydroxy-5'-phenylpregna-1,4-dieno[16α,17-b][1,4]dioxin-3,20-dione acetone solvate or dichloro methane solvate (1:1) is employed in all-in-solution ointments the isosorbide vehicle will be preferably employed in an amount within the range of from about 10 to about 25% by weight and more preferably within the range of from about 15 to about 25% by weight while the steroid will be employed in amounts ranging from about 0.001 to about 1% by weight.

Where 9α-fluoro-11β,16α,17,21-tetrahydroxypregna-1,4-diene-3,20-dione 16,17-acetonide is employed in all-in-solution ointments, the isosorbide vehicle will be preferably employed in an amount within the range of from about 10 to about 35% by weight and more preferably within the range of from about 15 to about 30% by weight while the amount of steroid employed will range from about 0.001 to about 1% by weight.

The lipophilic stick of the invention may contain from about 0.001 to about 2%, and preferably from about 0.001 to about 0.5% by weight active ingredient, and from about 15 to about 85% and preferably from about 15 to about 65% by weight of the isosorbide (regardless of which is employed) and from about 20 to about 50% and preferably from about 25 to about 45% by weight oleoginous material. Oleaginous materials which may be employed include high melting waxes, such as carnauba wax, in amounts ranging from about 6 to about 10% and preferably from about 7 to about 9%, beeswax in amounts ranging from about 14 to about 18% and preferably from about 15 to about 17%, as well as petrolatum in amounts ranging from about 2 to about 5% and preferably from about 3 to about 4%, and isostearyl neo pentanoate (Ceraphyl 375, Van Dyk) in amounts ranging from about 8 to about 11% and preferably from about 9 to about 10.5%.

In the case of ointments, lipophilic gels and sticks where the formulation is substantially free of water, the active ingredient will be dissolved in the isosorbide vehicle and, in part, in the oil material employed.

In general, the emulsifier-thickener suitable for use herein may comprise ethers of polyethylene glycol and fatty alcohols, such as, Promulgen, Robinson Wagner Co., which contains some unreacted cetyl and stearyl alcohol, and other non-ionic emulsifying waxes such as Polawax, Croda Co.

The same emulsifier-thickener used in the formulations of the invention may also be obtained by substituting the above-mentioned emulsifying waxes with a mixture of polyoxyethylene (20) stearyl alcohol ether (BRIJ 78, ICI) or polyoxyethylene (20) cetyl alcohol ether (BRIJ 58, ICI) with cetyl or stearyl alcohol. The ratio of the BRIJ or a mixture of the two BRIJ with the fatty alcohol or a mixture of the two alcohols should be within the range of from about 0.6 to about 3.5, preferably from about 1 to about 3.

Another emulsifier system suitable for use in the invention comprises a combination of glyceryl monostearate with polyoxyethylene sorbitan palmitate or stearate and cetyl or stearyl alcohol. For example, a cream or lotion containing 0.025% by weight 21-chloro-9α-fluoro-Δ⁴-pregnene-11β,16α,17α-triol-3,20-dione 16,17-acetonide in solution in dimethylisosorbide (30–50%), an oil-in-water cream, can be made with glyceryl monostearate (4.5–6%), cetyl or stearyl alcohol (9–11%) and Tween 60 (polyoxyethylene sorbitan monostearate 2.7–3.5%).

For 0.1% 21-chloro-9α-fluoro-Δ⁴-pregnene-11β,16α,17α-triol-3,20-dione 16,17-acetonide cream higher levels of isosorbide are required and Promulgen type emulsifier-thickeners are preferred. For topical steroids having higher solubility in isosorbide, such as, 21-chloro-9-fluoro-2',3'-dihydro-11β-hydroxy-5'-phenylpregna-1,4-dieno[16α,17-b][1,4]dioxin-3,20-dione acetone solvate or dichloro methane solvate (1:1) (approximately 40 mg/gm in dimethylisosorbide), a 0.1% all-in-isosorbide cream can be made with the second emulsion system containing glyceryl monostearate, cetyl alcohol and Tween 40 or 60.

It will also be appreciated that two or more materials may be employed to provide the emulsifying function and the thickening function. Thus, examples of emulsifying agents suitable for use herein include propylene glycol monostearate, as well as the non-ionic polyoxyalkylene derivatives of hexitol anhydride partial long chain fatty acid esters, e.g., the polyoxyalkylene derivatives of sorbitan monolaurate, sorbitan monopalmitate, sorbitan monostearate, sorbitan tristearate, sorbitan monooleate or sorbitan trioleate. These emulsifying agents are commercially available as Tween 20, 21, 40, 60, 65, 80, 81 and 85.

Thickeners suitable for use in combination with the above emulsifying agents include those conveniently employed in topical creams such as, for example, monoglycerides and fatty alcohols, fatty acid esters of alcohols having from about 3 to about 16 carbon atoms. Examples of suitable monoglycerides are glyceryl monostearate and glyceryl monopalmitate. Examples of fatty alcohols are cetyl alcohol and stearyl alcohol. Examples of suitable esters are myristyl stearate and cetyl stearate. The monoglyceride also functions as an auxilliary emulsifier. Other emollients or oleaginous materials which may be employed include petrolatum, glyceryl monooleate, myristyl alcohol and isopropyl palmitate.

The anti-foaming anti-whitening agent increases the elegancy of the cream or lotion and inhibits the formati on of a white soapy look upon rubbing the cream or lotion on the skin. An example of such a material suitable for use herein includes silicone fluid.

The cream, lotion or ointment may also contain an antioxidant such as butylated hydroxytoluene, butylated hydroxyanisole and the like for protecting the active ingredient against oxidation.

The preservative suitable for use herein may comprise propylene glycol or parabens (para-hydroxy benzoates) with the propylene glycol being preferred because of less incidence of skin sensitivity.

Examples of preferred formulations in accordance with the present invention include, but are not limited to, the following:

| Halcinonide Topical Cream, 0.025% | Ranges |
|---|---|
| Halcinonide, Micronized | 0.022–0.03 gm. |
| Dimethylisosorbide, I.C.I. | 40–50 gm. |
| Promulgen, Type D (Cetearyl alcohol & Ceteareth-20), Robinson-Wagner | 7–9 gm. |
| Petrolatum, U.S.P. | 10–20 gm. |
| *Methylparaben, U.S.P. | 0.10–0.20 gm. |
| *Propylparaben, U.S.P. | 0.01–0.05 gm. |
| Purified Water, q.s. | 100.0 gm. |
| Halcinonide Topical Cream, 0.1% | |
| Halcinonide, Micronized | 0.09–0.11 gm. |
| Dimethylisosorbide, I.C.I. | 50–60 gm. |
| Promulgen, Type D (Cetearyl alcohol & Ceteareth-20), Robinson-Wagner | 7.0–9.0 gm. |
| Petrolatum, U.S.P. | 10–20 gm. |
| *Methylparaben, U.S.P. | 0.10–0.2 gm. |
| *Propylparaben, U.S.P. | 0.01–0.05 gm. |
| Purified Water, q.s. | 100.0 gm. |
| Halcinonide Lotion 0.025% | |
| Halocinonide, Micronized | 0.02–0.03 gm. |
| Dimethylisosorbide, I.C.I. | 40–50 gm. |
| Stearyl Alcohol | 0.4–0.7 gm. |
| Cetyl Alcohol | 2.4–2.8 gm. |
| Tween 20 | 2.2–2.6 gm. |
| Span 40 | 0.4–0.6 gm. |
| *Methylparaben, U.S.P. | 0.1–0.2 gm. |
| *Propylparaben, U.S.P. | 0.01–0.05 gm. |
| Purified Water, q.s. | 100.0 gm. |
| Halcinonide Lotion 0.025% | |
| Halcinonide, Micronized | 0.022–0.03 gm. |
| Dimethylisosorbide, I.C.I. | 40–50 gm. |
| Promulgen, Type D (Cetearyl alcohol & Ceteareth-20), Robinson-Wagner | 1.0–3.0 gm. |
| Petrolatum, U.S.P. | 2.0–4.0 gm. |
| *Methylparaben, U.S.P. | 0.1–0.2 gm. |
| *Propylparaben, U.S.P. | 0.01–0.05 gm. |
| Purified Water, q.s. | 100.0 gm. |
| Halcinonide Lotion 0.1% | |
| Halcinonide, Micronized | 0.09–0.12 gm. |
| Dimethylisosorbide, I.C.I. | 50–60 gm. |
| Stearyl Alcohol | 0.4–0.6 gm. |
| Cetyl Alcohol | 2.4–2.8 gm. |
| Tween 20 | 2.0–3.0 gm. |
| Span 40 | 0.4–0.6 gm. |
| *Methylparaben, U.S.P. | 0.05–0.2 gm. |
| *Propylparaben, U.S.P. | 0.01–0.05 gm. |
| Purified Water, q.s. | 100.0 gm. |
| Halcinonide Lotion 0.1% | |
| Halcinonide, Micronized | 0.09–0.12 gm. |
| Dimethylisosorbide, I.C.I. | 50–60 gm. |
| Promulgen, Type D (Cetearyl alcohol & Ceteareth-20), Robinson-Wagner | 1.0–2.0 gm. |
| Petrolatum, U.S.P. | 2.0–4.0 gm. |
| *Methylparaben, U.S.P. | 0.1–0.2 gm. |
| *Propylparaben, U.S.P. | 0.01–0.05 gm. |
| Purified Water, q.s. | 100.0 gm. |
| Kenalog Lotion 0.1% | |
| Triamcinolone Acetonide, Micronized | 0.09–0.11 gm. |
| Dimethylisosorbide, I.C.I. | 35–45 gm. |
| Promulgen, Type D (Cetearyl alcohol & Ceteareth-20), Robinson-Wagner | 1.0–2.0 gm. |
| Petrolatum, U.S.P. | 2.0–4.0 gm. |
| *Methylparaben, U.S.P. | 0.1–0.2 gm. |
| *Propylparaben, U.S.P. | 0.01–0.05 gm. |
| Purified Water, q.s. | 100.0 gm. |
| Kenalog Lotion 0.1% | |
| Triamcinolone Acetonide, Micronized | 0.09–0.11 gm. |
| Dimethylisosorbide, I.C.I. | 35–45 gm. |
| Stearyl Alcohol | 0.4–0.6 gm. |
| Cetyl Alcohol | 2.4–2.8 gm. |
| Tween 20 | 2.0–3.0 gm. |
| Span 40 | 0.4–0.6 gm. |
| *Methylparaben, U.S.P. | 0.1–0.2 gm. |
| *Propylparaben, U.S.P. | 0.01–0.05 gm. |
| Purified Water, q.s. | 100.0 gm. |
| Econazole Cream 0.5% | |
| Econazole Nitrate | 0.5 gm. |
| Dimethylisosorbide, I.C.I. | 40–50 gm. |
| Petrolatum, U.S.P. | 3–5 gm. |
| Promulgen, Type D, Robinson-Wagner | 8–12 gm. |
| Purified Water, sufficient to make | 100.0 gm. |
| Econazole Lotion 0.5% | |
| Econazole Nitrate | 0.5 gm. |
| Dimethylisosorbide, I.C.I. | 47–52 gm. |
| Petrolatum, U.S.P. | 0.5–1.5 gm. |
| Promulgen, Type D, Robinson-Wagner | 3–5 gm. |
| Purified Water, sufficient to make | 100.0 ml. |

*Methylparaben preservatives may be replaced by 15% propylene glycol.

Since the solubility of econazole nitrate in water is approximately 1 mg/ml, the solubilized and available econazole nitrate in these preparations is about five (5) times or greater than that in a conventional lotion or cream.

| Kenalog Injection 0.2% (Veterinary) | Ranges |
|---|---|
| Triamcinolone Acetonide | 0.2 gm. |
| Dimethylisosorbide, I.C.I. | 50–70 gm. |
| Chlorobutanol, U.S.P. | 0.4–0.8 gm. |
| Pyrogen Free Triple Distilled Water, sufficient to make | 100.0 ml |
| Kenalog Eye Drop 0.02% (Sterile) | |
| Triamcinolone Acetonide | 0.02 gm. |
| Dimethylisosorbide, I.C.I. | 35–45 gm. |
| Methylparaben, U.S.P. | 0.1–0.2 gm. |
| Boric Acid, q.s. to adjust the isotonicity of the solution | |
| Distilled Water, sufficient to make | 100.0 ml |
| Kenalog-Neomycin Eye Drop 0.02% (Sterile) | |
| Triamcinolone Acetonide | 0.02 gm. |
| Neomycin Sulfate | 0.2–0.3 gm. |
| Dimethylisosorbide, I.C.I. | 34–45 gm. |
| Methylparaben, U.S.P. | 0.15–0.25 gm. |
| Boric Acid, q.s. to adjust the isotonicity of the solution | |
| Distilled Water, sufficient to make | 100.0 ml. |
| Kenalog Nose Drop 0.02% (Sterile) | |
| Triamcinolone Acetonide | 0.02 gm. |
| Phenylephrine HCl, U.S.P. | 0.25 gm. |
| Dimethylisosorbide, I.C.I. | 35–45 gm. |
| Methylparaben, U.S.P. | 0.1–0.2 gm. |
| Distilled Water, sufficient to make | 100.0 ml |
| Progesterone I.M. Injection, 25 mg/ml | |

-continued

| | |
|---|---|
| Progesterone | 2.5 gm. |
| Dimethylisosorbide, I.C.I. | 80–90 gm. |
| Chlorobutanol, U.S.P. | 0.4–0.8 gm. |
| Pyrogen free triple distilled water, sufficient to make | 100.0 ml |
| Testololactone I.M. Injection, 25 mg/ml | |
| $\Delta^1$-Testololactone | 2.5 gm. |
| Dimethylisosorbide, I.C.I. | 80–90 gm. |
| Chlorobutanol, U.S.P. | 0.4–0.8 gm. |
| Pyrogen free triple distilled water, sufficient to make | 100.0 gm. |

The following examples illustrate preferred embodiments of the present invention without, however, limiting the same thereto. All temperatures are expressed in degrees Centigrade.

Example 1

| Lotion, 0.025% (all-in-solution) | |
|---|---|
| 21-chloro-9α-fluoro-$\Delta^4$-pregnene-11β,16α, 17α-triol-3,20-dione 16,17-acetonide, Micronized | 0.025 gm. |
| Dimethylisosorbide U.S.P. | 45 gm. |
| Petrolatum, U.S.P. | 3 gm. |
| Promulgen, Type D (PEG fatty alcohol ether)-Cetearyl alcohol & Ceteareth-20 (Robinson-Wagner) | 1.5 gm. |
| Methylparaben, U.S.P. | 0.15 gm. |
| Propylparaben | 0.02 gm. |
| Purified Water, sufficient to make | 100.0 gm. |

The steroid and parabens are dissolved in dimethylisosorbide with gentle heat not over 90° C. The petrolatum and Promulgen are melted together and heated to 75°–80° C and then mixed with the above steroid solution. The resulting mixture is added to hot 75°–80° C purified water with vigorous agitation to emulsify. Agitation is continued until the temperature drops down to 48° C. Sufficient hot (48°–50° C) purified water is then added to make 100 gm. Mixing is then continued at a slow rate during the congealing stage until the temperature of the lotion reaches 42° C.

Example 2

| Halcinonide Lotion 0.025% | |
|---|---|
| Halcinonide, Micronized | 0.025 gm. |
| Dimethylisosorbide, I.C.I. | 45.0 gm. |
| Stearyl Alcohol | 0.5 gm. |
| Cetyl Alcohol | 2.6 gm. |
| Tween 20 | 2.4 gm. |
| Span 40 | 0.5 gm. |
| *Methylparaben, U.S.P. | 0.15 gm. |
| *Propylparaben, U.S.P. | 0.02 gm. |
| Purified Water, q.s. | 100.0 gm. |

*Methylparaben preservatives may be replaced by 15% propylene glycol.

The steroid is first dissolved in the isosorbide and then mixed with water at about 80°. Thereafter, the parabens are added to the mixture and dissolved therein with mixing. The stearyl and cetyl alcohols, Tween 20 and Span 40 are melted and added to the above mixtures with vigorous stirring while maintaining the mixture at 80° for 25–50 minutes to cause emulsification. The emulsion is cooled down to 40° while stirring gently until the emulsion congeals.

Example 3

| Halcinonide Lotion 0.1 | |
|---|---|
| Halcinonide, Micronized | 0.1 gm. |
| Dimethylisosorbide, I.C.I. | 55.0 gm. |
| Stearyl Alcohol | 0.5 gm. |
| Cetyl Alcohol | 2.6 gm. |
| Tween 20 | 2.4 gm. |
| Span 40 | 0.5 gm. |
| *Methylparaben, U.S.P. | 0.1 gm. |
| *Propylparaben, U.S.P. | 0.02 gm. |

Example 3-continued

| Halcinonide Lotion 0.1 | |
|---|---|
| Purified Water, q.s. | 100.0 gm.. |

*Methylparaben preservatives may be replaced by 15% propylene glycol.

The above lotion is prepared employing the procedure described in Example 2.

Example 4

| Halcinonide Lotion 0.1% | |
|---|---|
| Halcinonide, Micronized | 0.1 gm. |
| Dimethylisosorbide, I.C.I. | 55.0 gm. |
| Promulgen, Type D (Cetearyl alcohol & Ceteareth-20), Robinson-Wagner | 1.5 gm. |
| Petrolatum, U.S.P. | 3.0 gm. |
| *Methylparaben, U.S.P. | 0.15 gm. |
| *Propylparaben, U.S.P. | 0.02 gm. |
| Purified Water, q.s. | 100.0 gm. |

*Methylparaben preservatives may be replaced by 15% propylene glycol.

The above lotion is prepared employing the procedure of Example 1.

Example 5

| Kenalog Lotion 0.1% | |
|---|---|
| Triamcinolone Acetonide, Micronized | 0.1 gm. |
| Dimethylisosorbide, I.C.I. | 40.0 gm. |
| Stearyl Alcohol | 0.5 gm. |
| Cetyl Alcohol | 2.6 gm. |
| Tween 20 | 2.4 gm. |
| Span 40 | 0.5 gm. |
| *Methylparaben, U.S.P. | 0.15 gm. |
| *Propylparaben, U.S.P. | 0.02 gm. |
| Purified Water, q.s. | 100.0 gm. |

*Methylparaben preservatives may be replaced by 15% propylene glycol.

The above lotion is prepared employing the procedure of Example 2.

Example 6

| Kenalog Lotion 0.1% | |
|---|---|
| Triamcinolone Acetonide, Micronized | 0.1 gm. |
| Dimethylisosorbide, I.C.I. | 40.0 gm. |
| Promulgen, Type D (Cetearyl alcohol & Ceteareth-20), Robinson-Wagner | 1.5 gm. |
| Petrolatum, U.S.P. | 3.0 gm. |
| *Methylparaben, U.S.P. | 0.15 gm. |
| *Propylparaben, U.S.P. | 0.02 gm. |
| Purified Water, q.s. | 100.0 gm. |

*Methylparaben preservatives may be replaced by 15% propylene glycol.

The above lotion is prepared employing the procedure of Example 1.

Example 7

| Topical Cream, 0.1% (all-in-solution) | |
|---|---|
| Halcinonide | 0.1 gm. |
| Dimethylisosorbide | 55 gm. |
| Petrolatum, U.S.P. | 16.0 gm. |
| Promulgen, Type D (PEG fatty alcohol ether) | 8.0 gm. |
| Methylparaben | 0.15 gm. |
| Propylparaben | 0.02 gm. |
| Purified Water, sufficient to make | 100.0 gm. |

The steroid and parabens are dissolved in dimethylisosorbide with gentle heat, not over 90° C. Petrolatum and Promulgen D are melted together. After mixing, the mixture is added to the dimethylisosorbide solution with thorough mixing, maintaining the temperature at 75°–80° C. Water is heated to 80° C to form the aqueous phase which is added with vigorous agitation to the oil phase to emulsify. Agitation is continued until the temperature drops down to 48° C. Sufficient 50° C water is added to make 100 gm. Mixing is continued at a slow rate to congeal the mixture, until the temperature drops down to 42° C.

Example 8

| Halcinonide Topical Cream, 0.025% | |
|---|---|
| Halcinonide, Micronized | 0.025 gm. |
| Dimethylisosorbide, I.C.I. | 45.0 gm. |
| Promulgen, Type D (Cetearyl alcohol & Ceteareth-20), Robinson-Wagner | 8.0 gm. |
| Petrolatum, U.S.P. | 16.0 gm. |
| *Methylparaben, U.S.P. | 0.15 gm. |
| *Propylparaben, U.S.P. | 0.02 gm. |
| Purified Water, q.s. | 100.0 gm. |

*Methylparaben preservatives may be replaced by 15% propylene glycol.

The above cream is prepared according to the procedure of Example 7.

Example 9

| Econazole Cream 0.5% | |
|---|---|
| Econazole Nitrate | 0.5 gm. |
| Dimethylisosorbide, I.C.I. | 45.0 gm. |
| Petrolatum, U.S.P. | 4.0 gm. |
| Promulgen, Type D, Robinson-Wagner | 10.0 gm. |
| Purified Water, sufficient to make | 100.0 gm. |

The above cream is prepared according to the procedure of Example 7.

Example 10

| Econazole Lotion 0.5% | |
|---|---|
| Econazole Nitrate | 0.5 gm. |
| Dimethylisosorbide, I.C.I. | 48.0 gm. |
| Petrolatum, U.S.P. | 1.0 gm. |
| Promulgen, Type D, Robinson-Wagner | 4.0 gm. |
| Purified Water, sufficient to make | 100.0 ml. |

The above lotion is prepared according to the procedure of Example 1.

Example 11

| Kenalog Injection 0.2% (Veterinary) | |
|---|---|
| Triamcinolone Acetonide | 0.2 gm. |
| Dimeythylisosorbide, I.C.I. | 60.0 gm. |
| Chlorobutanol, U.S.P. | 0.5 gm. |
| Pyrogen Free Triple Distilled Water, sufficient to make | 100.0 ml. |

The above injectable is prepared by simply mixing the above ingredients.

Example 12

| Kenalog Eye Drop 0.02% (Sterile) | |
|---|---|
| Triamcinolone Acetonide | 0.02 gm. |
| Dimethylisosorbide, I.C.I. | 40.0 gm. |
| Methylparaben, U.S.P. | 0.15 gm. |
| Boric Acid, q.s. to adjust the isotonicity of the solution | |
| Distilled Water, sufficient to make | 100.0 ml. |

Example 13

| Kenalog-Neomycin Eye Drop 0.02% (Sterile) | |
|---|---|
| Triamcinolone Acetonide | 0.02 gm. |
| Neomycin Sulfate | 0.25 gm. |
| Dimethylisosorbide, I.C.I. | 40.0 gm. |
| Methylparaben, U.S.P. | 0.2 gm. |
| Boric Acid, q.s. to adjust the isotonicity of the solution | |
| Distilled Water, sufficient to make | 100.0 ml. |

Example 14

| Kenalog Nose Drop 0.02% (Sterile) | |
|---|---|
| Triamcinolone Acetonide | 0.02 gm. |
| Phenylephrine HCl, U.S.P. | 0.25 gm. |
| Dimethylisosorbide, I.C.I. | 40.0 gm. |

Example 14-continued

| Kenalog Nose Drop 0.02% (Sterile) | |
|---|---|
| Methylparaben, U.S.P. | 0.15 gm. |
| Distilled Water, sufficient to make | 100.0 ml. |

Example 15

| Progesterone I. M. Injection, 25 mg/ml | |
|---|---|
| Progesterone | 2.5 gm. |
| Dimethylisosorbide, I.C.I. | 85.0 gm. |
| Chlorobutanol, U.S.P. | 0.5 gm. |
| Pyrogen free triple distilled water, sufficient to make | 100.0 ml |

Example 16

| Testololactone I. M. Injection, 25 mg/ml | |
|---|---|
| $\Delta^1$-Testololactone | 2.5 gm. |
| Dimethylisosorbide, I.C.I. | 85.0 gm. |
| Chlorobutanol, U.S.P. | 0.5 gm. |
| Pyrogen free triple distilled water, sufficient to make | 100.0 ml. |

The above-described solutions are prepared by simply mixing the ingredients until a solution is formed.

Example 17

| Ointment, 0.025% (all-in-solution) | |
|---|---|
| 21-chloro-9α-fluoro-$\Delta^4$-pregnene-11β,16α,17α-triol-3,20-dione 16,17-acetonide, Micronized | 0.025 gm. |
| Dimethylisosorbide | 1 gm. |
| Titanium Dioxide | 0.5 gm. |
| Plastibase 50W (mineral oil) (95%) gelled with polyethylene (5%) sufficient to make 100.0 gm. | |

The steroid is dissolved in dimethylisosorbide with gentle heat not over 90° C. The solution is cooled to room temperature and titanium dioxide is dispersed homogeneously into the oil. The suspension is incorporated into the Plastibase by slow rate of mixing until homogeneous to form the ointment.

Example 18

| Lipophilic Clear Gel, 0.025% (all-in-solution) | |
|---|---|
| 21-chloro-9α-fluoro-$\Delta^4$-pregnene-11β,16α,17α-triol-3,20-dione 16,17-acetonide, Micronized | 0.025 gm. |
| Dimethylisosorbide | 1 gm. |
| Mineral Oil, U.S.P. | 80.375 gm. |
| Paraflint RG (High melting paraffin wax), Moore and Munger | 6.0 gm. |
| Span 65 (Sorbitan tristearate, ICI) | 3.6 gm. |

Paraflint RG and Span 65 are melted and heated to 100° C. The molten mixture is incorporated in hot (100° C) mineral oil and mixed well. The temperature of the oil is quickly brought to 50° C to form a gel.

The steroid is dissolved in dimethylisosorbide by gentle heat, the oil is cooled to room temperature and then is incorporated in the gel homogeneously.

Example 19

| Lipophilic Stick | |
|---|---|
| 21-chloro-9α-fluoro-$\Delta^4$-pregnene-11β,16α,17α-triol-3,20-dione 16,17-acetonide, Micronized | 0.1 gm. |
| Dimethylisosorbide | 2.5 gm. |
| Carnauba Wax | 8.0 gm. |
| Beeswax | 16.0 gm. |
| Petrolatum | 3.4 gm. |
| Ceraphyl 365, Van Dyk (Isostearyl Neo Pentanoate) | 10.0 gm. |

The steroid is dissolved in dimethylisosorbide with gentle heat not over 90° C. A molten mixture of the remaining ingredients is added to the above solution at 90° C. The mixture is poured into a mold and chilled to solidify the mixture to a stick.

What is claimed is:

1. A pharmaceutical composition comprising a pharmaceutical which is a steroid selected from the group consisting of 21-chloro-9α-fluoro-Δ⁴-pregnene-11β,16α,17α-triol-3,20-dione and its 16,17-acetonide; 21-chloro-9-fluoro-2',3'-dihydro-11α-hydroxy-5'-phenylpregna-1,4-dieno[16α, 17-b] [1,4]-dioxin-3,20-dione:acetone solvate and dichloromethane solvate (1:1); 9α-fluoro-11β,16α,17,21-tetrahydroxy-pregna-1,4-diene-3,20-dione 16,17-acetonide, 21-(acetyloxy)-9-fluoro-1',2',3',4'-tetrahydro-11β-hydroxypregna-1,4-dieno[16α,17-b]naphthalene-3,20-dione, progesterone, and Δ'-testololactone or a member selected from the group consisting of econazole or salts thereof, nystatin, neomycin, miconazole, gramicidin, halcinonide, triamcinolone acetonide, griseofulvin or mixtures thereof, and an isosorbide vehicle in which said pharmaceutical is at least partially soluble said isosorbide having the formula

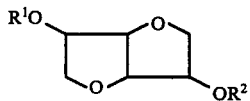

wherein R¹ and R² are the same or different and are selected from the group consisting of hydrogen or lower alkyl containing 1 to 5 carbons, at least one of R¹ and R² being lower alkyl.

2. The pharmaceutical composition as defined in claim 1 wherein said isosorbide vehicle is present in an amount within the range of from about 0.5 to about 95% by weight of the composition.

3. The pharmaceutical composition as defined in claim 1 wherein said isosorbide is dimethylisosorbide.

4. The pharmaceutical composition as defined in claim 1 in the form of an ointment, gel, lipophilic stick, lotion, cream or solution.

5. The composition as defined in claim 1 wherein said isosorbide vehicle is dimethylisosorbide.

6. The pharmaceutical composition as defined in claim 4 in the form of a cream or lotion wherein said steroid is present in an amount within the range of from about 0.005 to about 0.6% by weight of the composition, said isosorbide vehicle is present in an amount within the range of from about 30 to about 75% by weight of the composition, and further including an emulsifier-thickener present in an amount within the range of from about 1 to about 14% by weight of the composition, an oleaginous material or emollient present in an amount within the range of from about 0.2 to about 8% by weight of the composition, a preservative present in an amount within the range of from about 8 to about 50% by weight of the composition, and water present in an amount within the range of from about 30 to about 90% by weight water of the composition.

7. The composition as defined in claim 4 in the form of a lotion wherein said steroid is all-in-solution, said steroid being present in an amount within the range of from about 0.005 to about 0.6% by weight of the composition, said isosorbide being present in an amount within the range of from about 30 to about 75% by weight of the composition, and further including an emulsifier-thickener present in an amount within the range of from about 5 to about 14% by weight of the composition, an oleaginous material or emollient present in an amount within the range of from about 0.5 to about 6% by weight of the composition, a preservative present in an amount within the range of from about 10 to about 50% by weight of the composition, and water present in an amount within the range of from about 50 to about 90% by weight of the composition, and optionally including an anti-oxidant present in an amount within the range of from about 0.005 to about 0.04% by weight of the composition, and further optionally including an antiwhitening agent or anti-foaming agent present in an amount within the range of from about 0.2 to about 3% by weight of the composition.

8. The pharmaceutical composition as defined in claim 4 in the form of an ointment, gel or lipophilic stick wherein said pharmaceutical is a steroid present in an amount within the range of from about 0.005 to about 0.6% by weight of the composition, said isosorbide vehicle is present in an amount within the range of from about 0.5 to about 75% by weight of the composition, and further including an oleaginous material present in an amount within the range of from about 30 to about 99% by weight of the composition.

9. The composition as defined in claim 8 further including one or more antioxidants.

10. The pharmaceutical composition as defined in claim 4 in the form of a lipophilic stick, further including an oleaginous material, said isosorbide being present in an amount within the range of from about 15 to about 70% by weight of the composition and said oleaginous material being present in an amount within the range of from about 20 to about 50% by weight of the composition.

11. The composition as defined in claim 10 wherein said isosorbide is dimethylisosorbide and said oleaginous material is a mixture of carnauba wax, beeswax and petrolatum and further including isostearyl neopentanoate as a slip agent.

12. A method of treating dermatitis, which comprises administering topically an effective amount of a composition as defined in claim 4.

13. A method of treating dermatitis, which comprises administering topically an effective amount of a composition as defined in claim 6.

14. A method of treating dermatitis, which comprises administering topically an effective amount of a composition as defined in claim 8.

15. A method of treating dermatitis, which comprises administering topically an effective amount of a composition as defined in claim 10.

* * * * *

UNITED STATES PATENT AND TRADEMARK OFFICE
Certificate

Patent No. 4,082,881                                    Patented April 4, 1978

James Ling Chen and Jean M. Battaglia

Application having been made by James Ling Chen and Jean M. Battaglia, the inventors named in the patent above identified, and E. R. Squibb & Sons, Inc., Princeton, N.J., a corp. of Delaware, the assignee, for the issuance of a certificate under the provisions of Title 35, Section 256, of the United States Code, adding the name of Matthew J. Lynch as a joint inventor, and a showing and proof of facts satisfying the requirements of the said section having been submitted, it is this 29th day of April 1980, certified that the name of the said Matthew J. Lynch is hereby added to the said patent as a joint inventor with the said James Ling Chen and Jean M. Battaglia.

FRED W. SHERLING,
*Associate Solicitor.*